United States Patent
Hu et al.

(10) Patent No.: US 8,319,963 B2
(45) Date of Patent: Nov. 27, 2012

(54) COMPACT SENSOR SYSTEM

(75) Inventors: Min Hu, Sunnyvale, CA (US); Wei Wu, Palo Alto, CA (US); Fung Suong Ou, Palo Alto, CA (US); Zhen Peng, PFoster City, CA (US); Zhiyong Li, Redwood City, CA (US); R. Stanley Williams, Portola Valley, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 383 days.

(21) Appl. No.: 12/772,063

(22) Filed: Apr. 30, 2010

(65) Prior Publication Data
US 2011/0267610 A1 Nov. 3, 2011

(51) Int. Cl.
*G01J 3/44* (2006.01)
(52) U.S. Cl. ...................................................... 356/301
(58) Field of Classification Search .................. 356/301
See application file for complete search history.

(56) References Cited

U.S. PATENT DOCUMENTS

| | | | |
|---|---|---|---|
| 6,888,854 B2 * | 5/2005 | Margalit | 372/6 |
| 7,136,160 B2 * | 11/2006 | Wang | 356/301 |
| 7,151,599 B2 | 12/2006 | Islam et al. | |
| 7,351,588 B2 * | 4/2008 | Poponin | 436/171 |
| 7,511,808 B2 | 3/2009 | Tong et al. | |
| 7,532,656 B2 | 5/2009 | Yang et al. | |
| 2008/0079104 A1 | 4/2008 | Stewart et al. | |
| 2012/0113419 A1 * | 5/2012 | Wang et al. | 356/301 |

FOREIGN PATENT DOCUMENTS
WO WO-2008073529 6/2008
* cited by examiner

*Primary Examiner* — Layla Lauchman

(57) ABSTRACT

A compact sensor system comprising: an analysis cell configured for photon-matter interaction, where photons are received from a light source; and an integrated-optical spectral analyzer configured for identifying a set of frequencies, the integrated-optical spectral analyzer comprising: a waveguide coupled with the analysis cell, the waveguide configured for propagating a set of frequencies through the waveguide; one or more ring resonators coupled with the waveguide, the one or more ring resonators comprising a predetermined bandwidth and configured for capturing the set of frequencies corresponding to frequencies within the predetermined bandwidth; and one or more frequency detectors coupled with the one or more tunable ring resonators, the one or more frequency detectors configured for generating electrical signals that identify each of the set of frequencies.

16 Claims, 6 Drawing Sheets

COMPACT SENSOR SYSTEM

FIELD

Embodiments of the present technology relate to compact molecular sensing system based on optical spectroscopic technique.

BACKGROUND

Raman spectroscopy has emerged as a leading technique for the analysis of the structure of inorganic materials and complex organic molecules. Scientists engaged in the application of Raman spectroscopy have found that by decorating a surface, upon which a molecule is later adsorbed, with a thin layer of a metal in which surface plasmons have frequencies in a range of electromagnetic radiation used to excite such a molecule and in which surface plasmons have frequencies in a range of electromagnetic radiation emitted by such a molecule, it is possible to enhance the intensity of a Raman spectrum of such a molecule. This technique has been termed surface enhanced Raman spectroscopy (SERS).

In addition, spectroscopists utilizing spectroscopic techniques for the analysis of molecular structures have a continuing interest in improving the sensitivity of their spectroscopic techniques. Not only is improved sensitivity desirable for reducing the time of analysis, but also improved sensitivity can provide previously unachievable results. For example, improved sensitivity is directly related to lower detectability limits for previously undetected molecular constituents. Thus, scientists engaged in the application of Raman spectroscopy are motivated to improve the sensitivity of SERS for the detection of molecules and the spectral signatures of moieties in these molecules.

BRIEF DESCRIPTION OF THE DRAWINGS

The accompanying drawings, which are incorporated in and form a part of this specification, illustrate embodiments of the present technology for a system for improving Raman detection efficiency, together with the description, serve to explain principles discussed below.

The drawings referred to in this description should not be understood as being drawn to scale unless specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Overview

Embodiments of the present technology combine the advantages of nanostructure arrays and ring resonators to create a high performance sensor system. By designing the ring resonator with a matching optical frequency with characteristic Raman emission frequency, the sensitivity of the device can be significantly improved. Additionally, the use of the nanostructure arrays and ring resonators enables the technology described herein to be fabricated in a more compact miniaturized manner.

Embodiments of the present technology provide a compact sensor system that combines unique nanostructures for a highly enhanced light-matter interaction with a combined ring resonator/detector as an integrated optical spectral analyzer. Consequently, embodiments of the present invention are expected to provide enhanced detectabilibilty along with miniaturization, because of the synergy between the nanostructure and the combined ring resonator/detector. Therefore, the inventors expect many novel applications to materialize for the compact sensor system, here to fore unprecedented in the field of spectroscopy.

Compared with present day technology, since the overall size of embodiments of the present technology has decreased, it is possible to transport the compact sensor system to locations and environments that originally were too small for a larger system, such as a spectrometer Additionally, the present technology may be used for small molecule detection. Further, explosive species or biological species in the food industry and the biochemical industry and the medical field may be detected. Thus, the spectrometer of the present technology is very sensitive and may even detect down to a single molecule.

Figure 1:
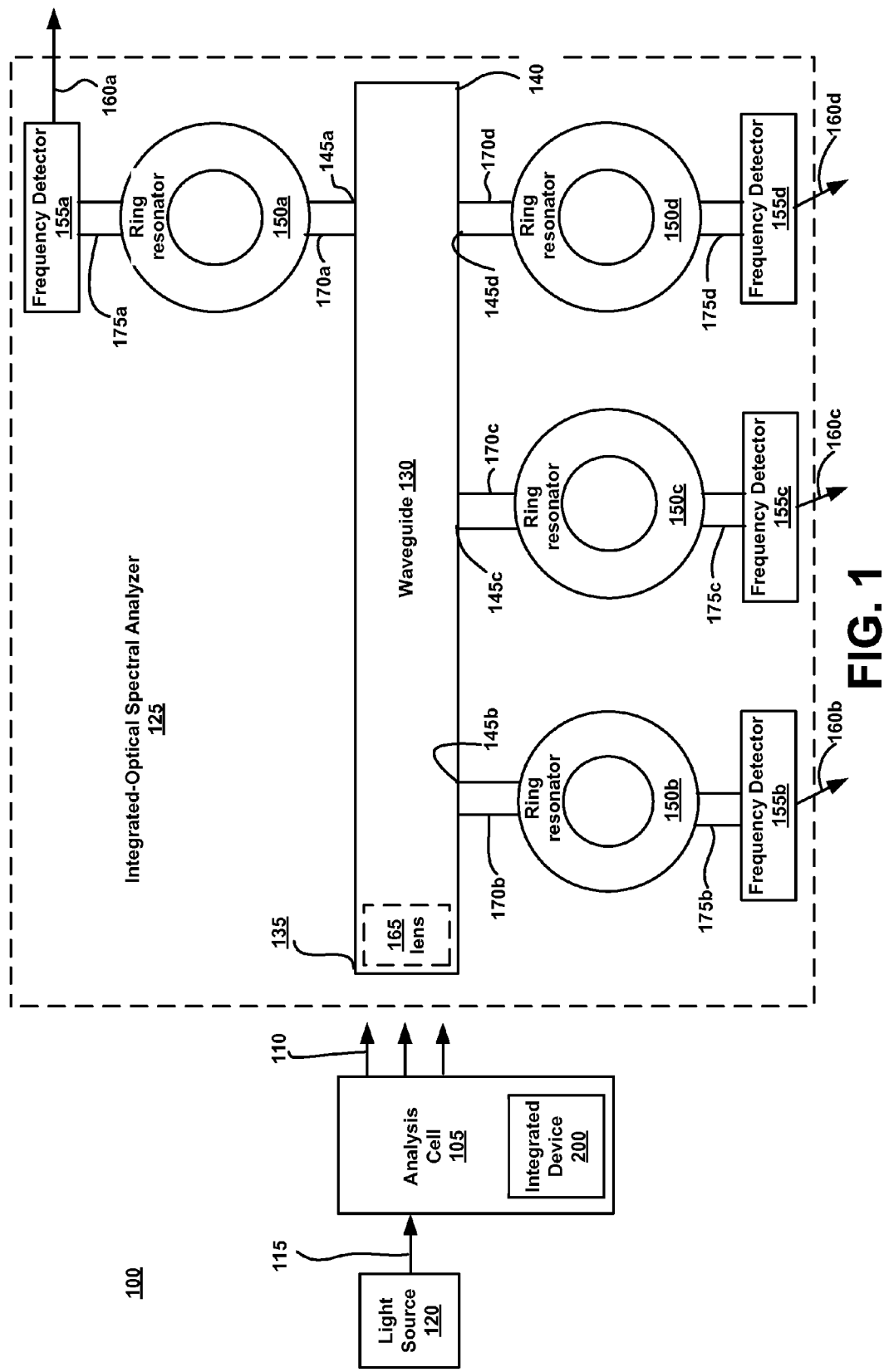
FIG. 1 illustrates an example of a compact sensor system, in accordance with an embodiment of the present technology.

Embodiments of the present technology comprise an analysis cell coupled with an integrated-optical spectral analyzer. FIG. 1 depicts a compact sensor system 100 for improving Raman detection efficiency. Compact sensor system 100 includes an analysis cell 105 optically coupled with an integrated-optical spectral analyzer 125. The analysis cell 105 is free-standing from the integrated-optical spectral analyzer 125. In another embodiment, analysis cell 105 is physically coupled with integrated-optical spectral analyzer 125. Analysis cell 105 comprises integrated device 200, which is described below. Integrated-optical spectral analyzer 125, also described below, comprises waveguide 130, one or more ring resonators 150a, 150b, 150c and 150d, and one or more frequency detectors 155a, 155b, 155c and 155d.

A discussion of the analysis cell is below, followed by a discussion of an integrated-optical spectral analyzer coupled therewith. A description of a method for improving Raman detection efficiency then follows.

Analysis Cell 105

Referring to FIG. 1, in one embodiment, analysis cell 105 is configured for photon-matter interaction 110, involving the photons of the light 115 received from the light source 120. In embodiments of the present technology, light source 120 is a type of solid state laser. In one embodiment, the solid state laser is a light emitting diode (LED). In other embodiments, other types of light sources 120 may be used, such as but not limited to, plasmonic lasers and cavity lasers. In one embodiment, light source 120 is coupled with analysis cell 105, while in another embodiment, light source 120 is free standing from analysis cell 105. In embodiments of the present technology, the optical range of light 115 from light source 120 varies from ultraviolet to infrared.

Photon-matter interaction 110 comprises different types of emissions, such as Raman, fluorescence, etc. In embodiments of the present technology, light 120 may undergo an elastic or an inelastic scattering process, which can also be directly analyzed by the compact sensor system. As previously stated, analysis cell 105 comprises integrated device 200.

Figure 2:
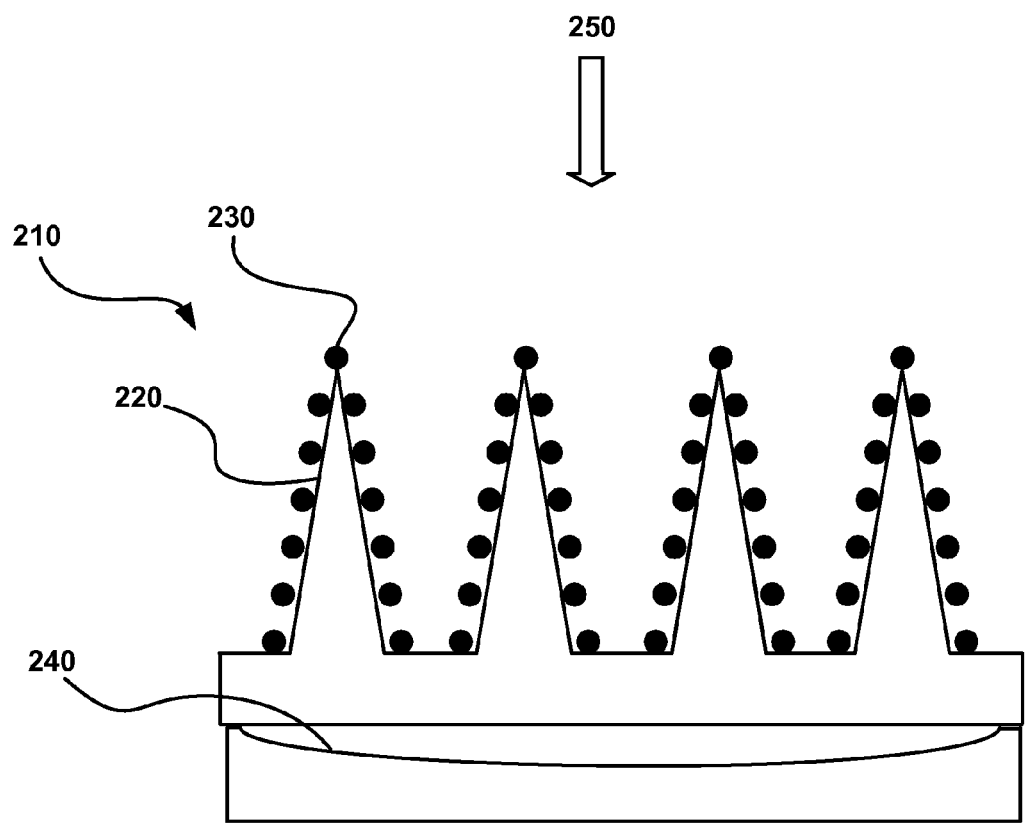
FIGS. 2-4 illustrate examples of an integrated device, in accordance with an embodiment of the present technology.

FIG. 2 depicts an integrated device 200 for enhancing signals in Surface Enhanced Raman Spectroscopy (SERS). Integrated device 200 includes an array of nanostructures 210, SERS active nanoparticles 230 and a mirror 240. Integrated device 200 optionally includes a resonant grating (e.g., resonant grating 350 of FIG. 3), which will be described in detail below.

In one embodiment, nanostructures 210 are three dimensional. For example, nanostructures 210 comprise a plurality of cones 220 or a plurality of substantially cone-shaped features (e.g., nanograss). In various embodiments, nanostructures 210 are any shape that is compatible with enhancing signals in SERS. In various examples, nanostructures 210 can be, but are not limited to, positive cone shapes, negative cone shapes, pillar shaped, mushroom shaped, teepee shaped, hemisphere shaped, pyramid shaped, columnar shaped, and the like.

In another embodiment, nanostructures 210 are a periodic array of nanostructures. For example, nanostructures 210 are regularly spaced along the x-direction (as shown in FIGS. 2-5) and regularly spaced in the z-direction (into the page). The height of nanostructures 210 (y-direction) are substantially equal. Moreover, the height and base dimensions can be selected to support guided-mode resonance for various light 250 wavelengths.

Nanostructures 210 are configured to allow light 250 to pass through. In various embodiments, nanostructures 210 are comprised of a translucent or transparent material. For example, nanostructures 210 are comprised of glass or polymer. The transparent or translucent property of the material of nanostructures 110 enhances signals in SERS, which will be described in detail below.

SERS active nanoparticles 230 are disposed on at least a portion of nanostructures 110. In one embodiment, SERS active nanoparticles 230 are deposited (e.g., electron beam deposition) metal particles. For example, SERS active nanoparticles 230 can be, but are not limited to, silver, gold, platinum and copper.

FIGS. 2-5 depict SERS active nanoparticles 130 evenly dispersed on the outer surface of nanostructures 210. However, in various embodiments, SERS active nanoparticles 230 can be randomly dispersed on the outer surface of nanostructures 210. Also, SERS active nanoparticles 230 cover the entire outer surface of nanostructures 210. In yet another embodiment, the SERS active metal nanostructure can be selectively dispersed on the tip of the nanostructures 210.

Figure 3:
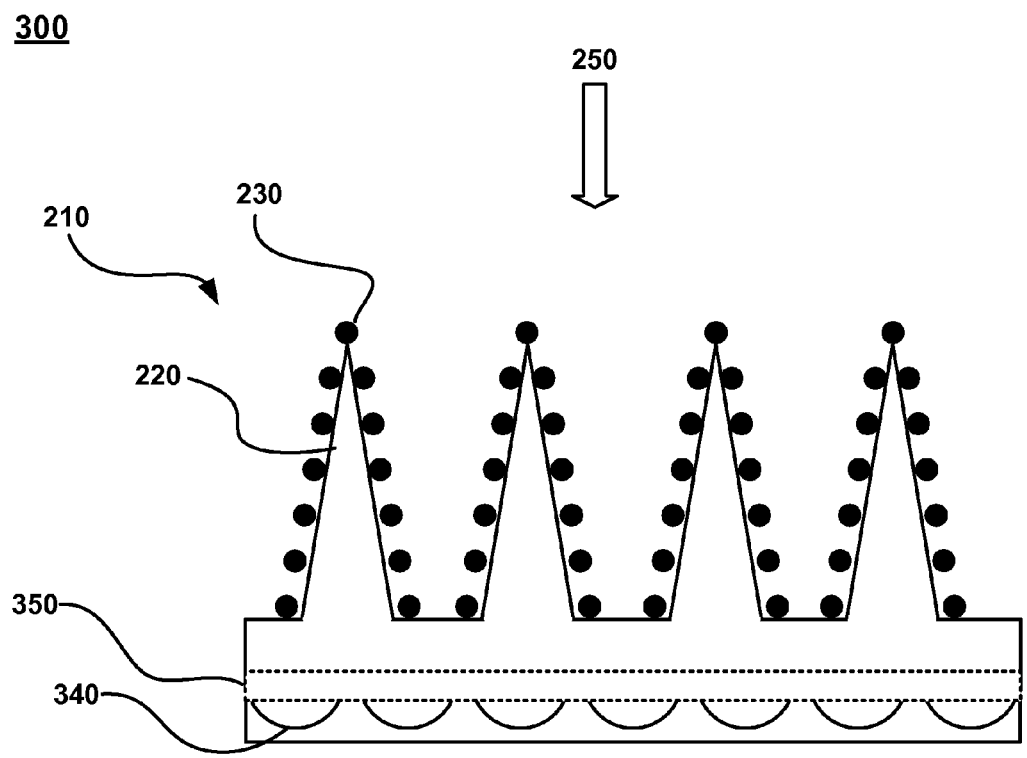

Mirror 240 is integrated below a base of nanostructures 210. Mirror 240 is configured to reflect light that passes through the material of the nanostructures 210 back into nanostructures 210. In one embodiment, mirror 240 is a single concave mirror disposed and integrated below a base of nanostructures 210. In another embodiment, as depicted in FIG. 3, a plurality of concave mirrors 340 are integrated below a base of nanostructures 210.

During use, light 250 (e.g., Raman-excitation light) is emitted towards integrated device 200 to facilitate in detecting analyte molecules (not shown) located on, or in close proximity to, SERS active nanoparticles 230. As light 250 is incident upon the analyte molecules, a Raman-scattered light is reflected off of the analyte molecules. Additionally, the combination of SERS active nanoparticles 130 and nanostructures 210 cause enhancement of the intensity of the Raman-scattered light from the analyte molecules.

Moreover, as light 250 passes through nanostructures 210, light 250 reflects off of mirror 240 and back into and subsequently out of nanostructures 210. As a result, nanoparticles 130 and analyte molecules are excited once again (e.g., double excitation). Thus, the 230 of the Raman-scattered light from the analyte molecules is enhanced even further.

In particular, the wavelengths selected for light 250 cause analyte molecules to emit a Raman spectrum of Raman scattered light over a range of wavelengths. The intensity of the Raman scattered light may also be enhanced as a result of two mechanisms associated with the SERS active nanoparticles 230 (e.g., Raman active material). The first mechanism is enhanced electromagnetic field produced at the surface of the SERS active nanoparticles 230. As a result, conduction electrons in the metal surfaces of the SERS active nanoparticles 230 are excited into an extended surface excited electron state called a "surface Plasmon polariton."

Analyte molecules adsorbed on or in close proximity to the SERS active nanoparticles 230 experience a relatively strong electromagnetic field. Molecular vibrational modes directed normal to the SERS active nanoparticles 230 are most strongly enhanced. The intensity of the surface Plasmon polariton resonance depends on many factors including the wavelengths of light 250. The second mode of enhancement, charge transfer, may occur as a result of the formation of a charge-transfer complex between the surfaces of the SERS active nanoparticles 230 and the analyte molecules. The electronic transitions of many charge transfer complexes are typically in the visible range of the electromagnetic spectrum.

Still referring to FIG. 2, in various embodiments, mirror 240 increases the effective numeric aperture. For example, the higher order of numeric aperture, the increased ability to collect a higher cone angle of light 250. Also, mirror 240 can collect certain angle distribution of Raman scattered light and focus it into a narrower distribution angle.

FIG. 3 depicts an integrated device 300, in accordance to an embodiment of the present invention. Integrated device 300 is similar to integrated device 200 and includes an array of nanostructures 210 and SERS active nanoparticles 230. However, integrated device 300 includes a plurality of concave mirrors 340. Integrated device 300 optionally includes a resonant grating 350.

Concave mirrors 340 function similarly as concave mirror 2440, as described above. In particular, concave mirrors 340 are integrated below a base of nanostructures 210. Concave mirrors 340 are configured to reflect light that passes through the material of the nanostructures 210 back into nanostructures 210.

Resonant grating 350 is integrated below a base of nanostructures 210. Resonant grating 350 is configured to establish a guided-mode resonance with light passing through integrated device 300. Resonant grating 350 can be, but is not limited to, a dielectric grating or a metal grating.

Resonant grating 350 supports guided-mode resonance with certain wavelengths of light 250. Guided-mode resonance enhances, or increases, the intensity of the associated electro magnetic field. As a result, Raman-excitation light can be emitted or coupled out through nanostructures 210. The enhanced electromagnetic field also interacts with the Raman-active material to further enhance this emission process for analyte molecules located on, or in close proximity to, SERS active nanoparticles 230.

Figure 4:
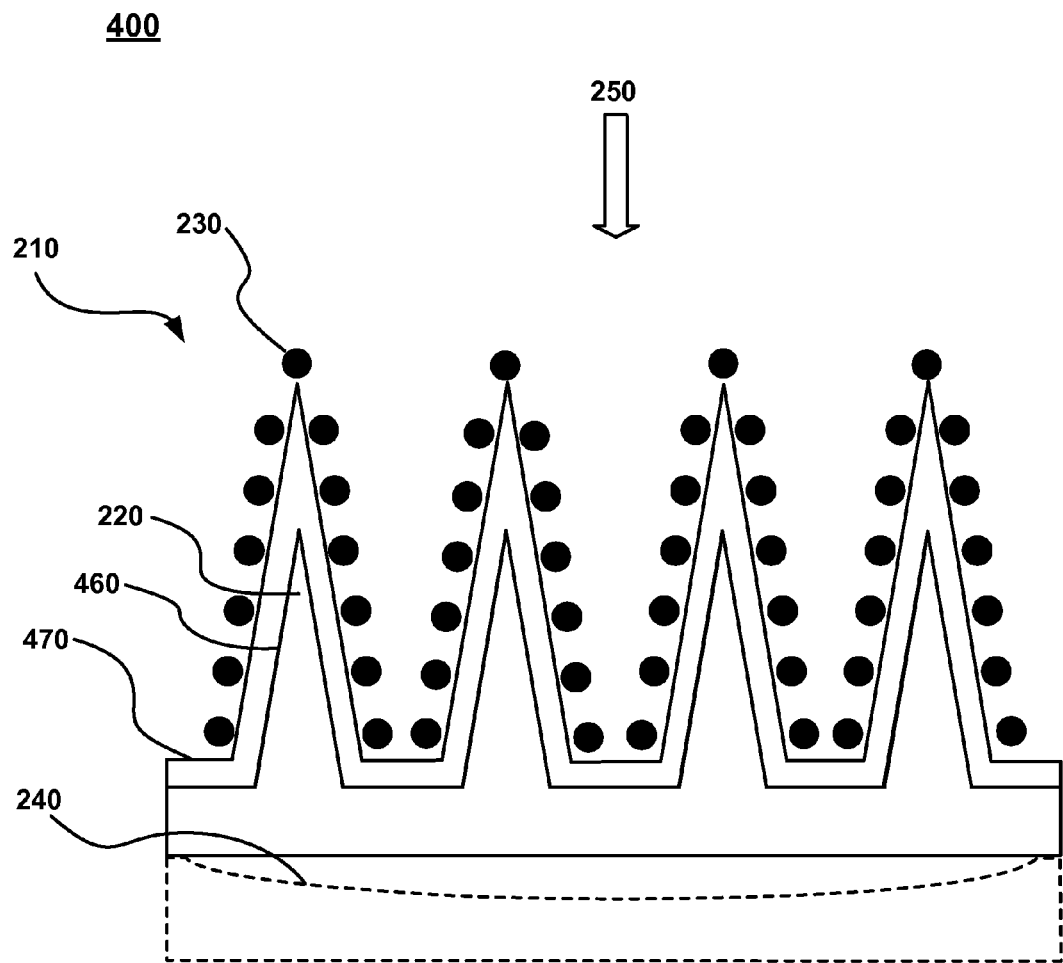

FIG. 4 depicts an integrated device 400, in accordance to an embodiment of the present invention. Similar to FIGS. 2 and 3, integrated device 400 includes an array of nanostructures 210 and SERS active nanoparticles 230. However, integrated device 400 also includes a thin metal layer 460 and a thin dielectric layer 470. Integrated device 400 optionally includes any combination of resonance grating 350, concave mirror 2440 and/or a plurality of concave mirrors 340, as described above.

Metal layer 460 is disposed on a surface of nanostructures 210. Metal layer 460 is configured to reflect light 250 and also allow light 250 to pass through. In various embodiments, metal layer 460 has a thickness in the range of about 5 nanometers (nm) to 200 nm. Also, metal layer 460 can be, but is not limited to, silver, gold and copper.

Metal layer 460 is transparent or translucent. Surface Plasmon of metal layer 460 can be excited due to light 250. Therefore, metal layer 460 can create a strong excitation signal.

Dielectric layer 470 is disposed on a surface of metal layer 460. Dielectric layer 470 is configured to allow light 250 to pass through. Dielectric layer 470 has a thickness that allows analyte molecules to be subject to any plasmonic field on metal layer 460. In one embodiment, dielectric layer 470 is a material (e.g., analyte molecules).

Figure 5:
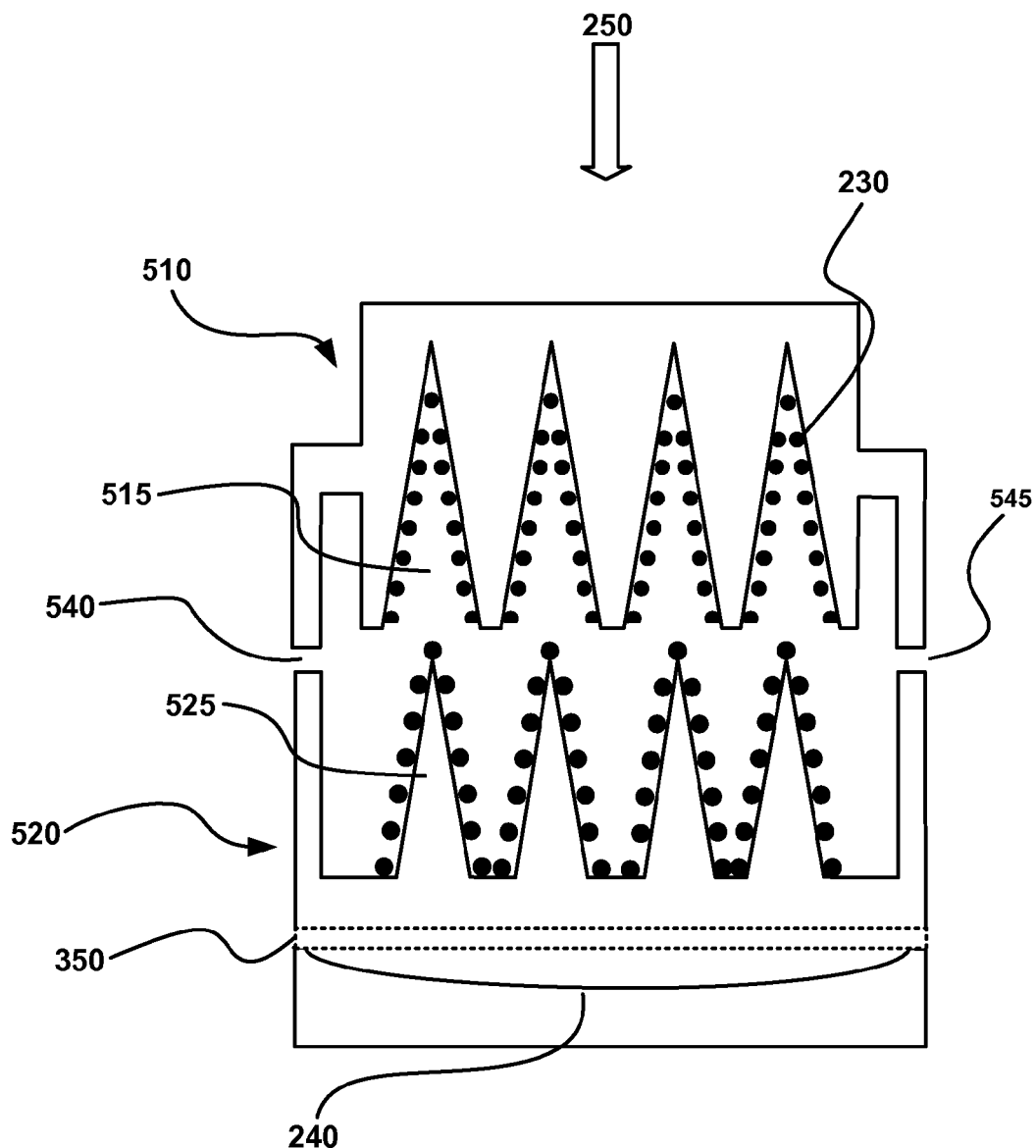
FIG. 5 illustrates an enclosure, in accordance with an embodiment of the present technology.

FIG. 5 depicts an enclosure 500 for enhancing signals in SERS, in accordance to an embodiment of the present invention. Enclosure 500 includes first array of nanostructures 510, second array of nanostructures 520, mirror 240, SERS active nanoparticles 230, inlet 540 and outlet 545. Enclosure 500 optionally includes resonance grating 350, as described above.

First array of nanostructures 510 includes a plurality of negative cones 515. In contrast, second array of nanostructures 520 includes a plurality of positive cones 525. In various embodiments, first and second array of nanostructures can include any combination of positive nanostructures (e.g., cones) or negative nanostructures. For example, first array of nanostructures 510 are negative cones and second array of nanostructures 520 are negative cones.

First and second array of nanostructures 510 and 520 are configured to allow light 250 to pass through. In various embodiments, first and second array of nanostructures 510 and 520 are comprised of a translucent or transparent material. For example, first and second array of nanostructures 510 and 520 are comprised of glass or polymer. It should be appreciated that first and second array of nanostructures enhance signals related to SERS, as described above.

In one embodiment, first array of nanostructures 510 face second array of nanostructures 520. In another embodiment, first array of nanostructures 510 are aligned with second array of nanostructures 520. For example, a peak of cone 525 is aligned with a negative peak of negative cone 515.

Mirror 240 is integrated below a base of second array of nanostructures 520. Mirror is configured to reflect light 250 that passes through both first and second array of nanostructures 510 and 520 back into first and second array of nanostructures 510 and 520. In various embodiments, mirror 240 is a single concave mirror or a plurality of concave mirrors (e.g., mirrors 340 of FIG. 3).

In various embodiments, the mirror(s) can be, but are not limited to, convex mirror(s), cylindrical mirror(s) and any combination thereof.

During use, light 250 (e.g., Raman-excitation light) is emitted towards integrated device 200 to facilitate in detecting analyte molecules (not shown) located on, or in close proximity to, SERS active nanoparticles 230. The analyte molecules are provided through inlet 540 and exit at outlet 545. In one embodiment, analyte molecules are introduced into enclosure 500 via gas flow through inlet 540 and outlet 545.

As light 250 is incident upon the analyte molecules, a Raman-scattered light is reflected off of the analyte molecules. Additionally, the combination of SERS active nanoparticles 230 and first and second array of nanostructures 510 and 520 cause enhancement of the intensity of the Raman-scattered light from the analyte molecules.

Moreover, as light 250 passes through first and second array of nanostructures 510 and 520, light 250 reflects off of mirror 240 and back into and subsequently out of first and second array of nanostructures 510 and 520. As a result, SERS active nanoparticles 230 and analyte molecules are excited once again (e.g., double excitation). Thus, the intensity of the Raman-scattered light from the analyte molecules is enhanced even further.

In one embodiment, inlet 540 and outlet 545 are closed after analyte molecules are introduced in enclosure 540. As a result, Raman-scattered light from the analyte molecules is enhanced even further.

In various embodiments, a plurality of enclosures 500 are stacked up with one another. It should also be appreciated that any combination of array of nanostructures and/or any combination of enclosures (e.g., enclosure 500) can be combined to facilitate in enhancing signals in SERS.

In various embodiments, array of nanostructures (e.g., positive array of nanostructures and/or negative array of nanostructures) can be created by black silicone (black Si) that includes an array of nanostructures. In such embodiments, black Si can be used as a mold. The array of nanostructures on the black Si is imprinted onto a first substrate, such as glass or polymer. As a result, a negative array of nanostructures are created on the first substrate. The first substrate can be utilized as a mold and/or an array of negative nanostructures for use in SERS.

When used as a mold, a positive array of nanostructures can be imprinted on a second substrate, such as glass or polymer. As a result, the array of positive nanostructure on the second substrate can be utilized as an array of positive nanostructures for use in SERS. It should be appreciated that the array of nanostructures can be large area (e.g., larger than a 6 inch wafer).

The process of creating array of nanostructures can be, but is not limited to, nanoimprint lithography (NIL).

Integrated-Optical Spectral Analyzer

Referring now to FIG. 1, an integrated-optical spectral analyzer (IOSA) 125 is shown, according to one embodiment of the present technology. IOSA 125 is configured for identifying a set of frequencies of luminescence 110. IOSA 125 comprises waveguide 130, as known in the art, which is coupled with one or more ring resonators 150a, 150b, 150c and 150d (hereinafter, "150a-150d"), which is in turn coupled with one or more frequency detectors 155a, 155b, 155c and 155d (hereinafter, "155a-155d"). In embodiments of the present technology, waveguide 130 is fabricated from material commonly used in the art for fabricating waveguides. For example, in one embodiment, waveguide 130 is fabricated from silicon oxide.

In one embodiment, waveguide 130 includes first end 135 and second end 140 with ring resonator integration sites, shown in FIG. 1 as 145a, 145b, 145c and 145d (hereinafter, "145a-145d"). It is appreciated that there may be more or less ring resonator integration sites along waveguide 130 than that shown in FIG. 1.

In one embodiment, waveguide is optically coupled via a lens 135 with the analysis cell 105. The lens 135 is coupled with the first end 165 of the waveguide 130 and is configured for capturing the luminescence 110 generated by the analysis cell 105. In one embodiment, waveguide 130 is configured for propagating the set of frequencies through the waveguide 130 from the analysis cell 105 to the second end 140.

In one embodiment, one or more tunable ring resonators 150a-150d are coupled with one or more ring resonator integration sites 145a-145d. Typically, an optical ring resonator consists of a waveguide in a closed loop coupled to one or more input/output waveguides. When light of the appropriate wavelength is coupled to the loop by the input waveguide, it builds up in intensity over multiple round-trips due to constructive interference. The light can then be picked up by a device, such as a frequency detector of frequency detectors 155a-155d.

In one embodiment, the one or more tunable ring resonators 150a-150d comprise a predetermined bandwidth and are configured for capturing the set of frequencies from the luminescence 110 corresponding to frequencies within the predetermined bandwidth. For example, ring resonator 150a may be tuned to comprise a bandwidth including a frequency of 785 nanometers. Suppose that the photons of the luminescence 110 that are propagated through waveguide 130 include a frequency of 785. Ring resonator 150a would then capture this frequency of 785 nanometers.

Examples of other bands of frequency that may be provided by the light source 120 during spectroscopy include but are not limited to the following: 415 nanometers, 572 nanometers, 673 nanometers, 785 nanometers and 1064 nanometers. One advantage of the use of the one or more ring resonators 150a-150d is that their Q factor is extremely high. The ring resonators 150a-150d may be tuned to a very narrow bandwidth, and thus, a very narrow range of frequencies. Furthermore, in one embodiment, several ring resonators may be finely tuned to cover a small range of wavelengths. The bandwidth of these same ring resonators may be overlapped, thus covering a continuous wavelength band.

Ring resonators may be fabricated in different shapes. For example, in one embodiment, a ring resonator may be of a circular shape. In another embodiment, a ring resonator may be that of an oval shape.

In one embodiment, the one or more frequency detectors 155a-155d (also known in the art as "waveguide detectors") are coupled with the one or more tunable ring resonators 150a-150d. While the one or more tunable ring resonators 150a-150d are pre-tuned to a certain frequency, one or more frequency detectors 155a-155d are sensitive to a certain band of frequency. The one or more frequency detectors 155a-155d are configured for generating electrical signals 160a, 160b, 160c and 160d (hereinafter, "160a-160d") that identify each of the set of frequencies of the luminescence 110 captured by the ring resonators 150a-150d.

In embodiments of the present technology, waveguide 130 is coupled with one or more ring resonators 150a-150d via one or more waveguide connectors 170a, 170b, 170c and 170d (hereinafter, "170a-170d"). Furthermore, one or more ring resonators 150a-150d are coupled with one or more frequency detectors 155a-155d via one or more waveguide connectors 175a, 175b, 175c and 175d (hereinafter, "175a-175d"). The waveguide connectors 170a-170d may be fabricated out of the same material of which waveguides are typically fabricated. The waveguide connectors 170a-170d are configured for propagating luminescence 110 therethrough.

In one embodiment, a monolithic integrated optical spectrometer comprises: a waveguide 130 comprising a first end 135 and a second end 140 and one or more ring resonator integration sites 145a-145d therebetween. The first end 135 of the waveguide 130 is coupled with a resonant grating 350 of FIG. 3 of an integrated device 200 of an analysis cell 105. The waveguide 130 is configured for propagating a set of frequencies through the waveguide 130 from the integrated device 200 to the second end 140. The integrated device 200 is configured for enhancing signals in Surface Enhanced Raman Spectroscopy.

The term of, "integrated optical" refers to integrated components integrated on a monolithic substrate analogous to an integrated electrical circuit (i.e. or known in the art as an IC chip) of a monolithic substrate.

Furthermore, in one embodiment the monolithic integrated optical spectrometer comprises one or more tunable ring resonators 1450a-150d coupled with the one or more ring resonator integration sites 145a-145d of the waveguide 130. The one or more tunable ring resonators 145a-145d comprises a predetermined bandwidth and is configured for capturing the set of frequencies corresponding to frequencies within the predetermined bandwidth. In one embodiment, the monolithic integrated optical spectrometer further includes one or more frequency detectors 155a-155d that are coupled with the one or more tunable ring resonators 150a-150d. The one or more frequency detectors 155a-155d are configured for generating signals that identify each of the set of frequencies.

Example Operation of Sensor Device

More generally, in embodiments in accordance with the present technology, compact sensor device 100 is utilized to improve the sensitivity of the molecular detection.

Figure 6:
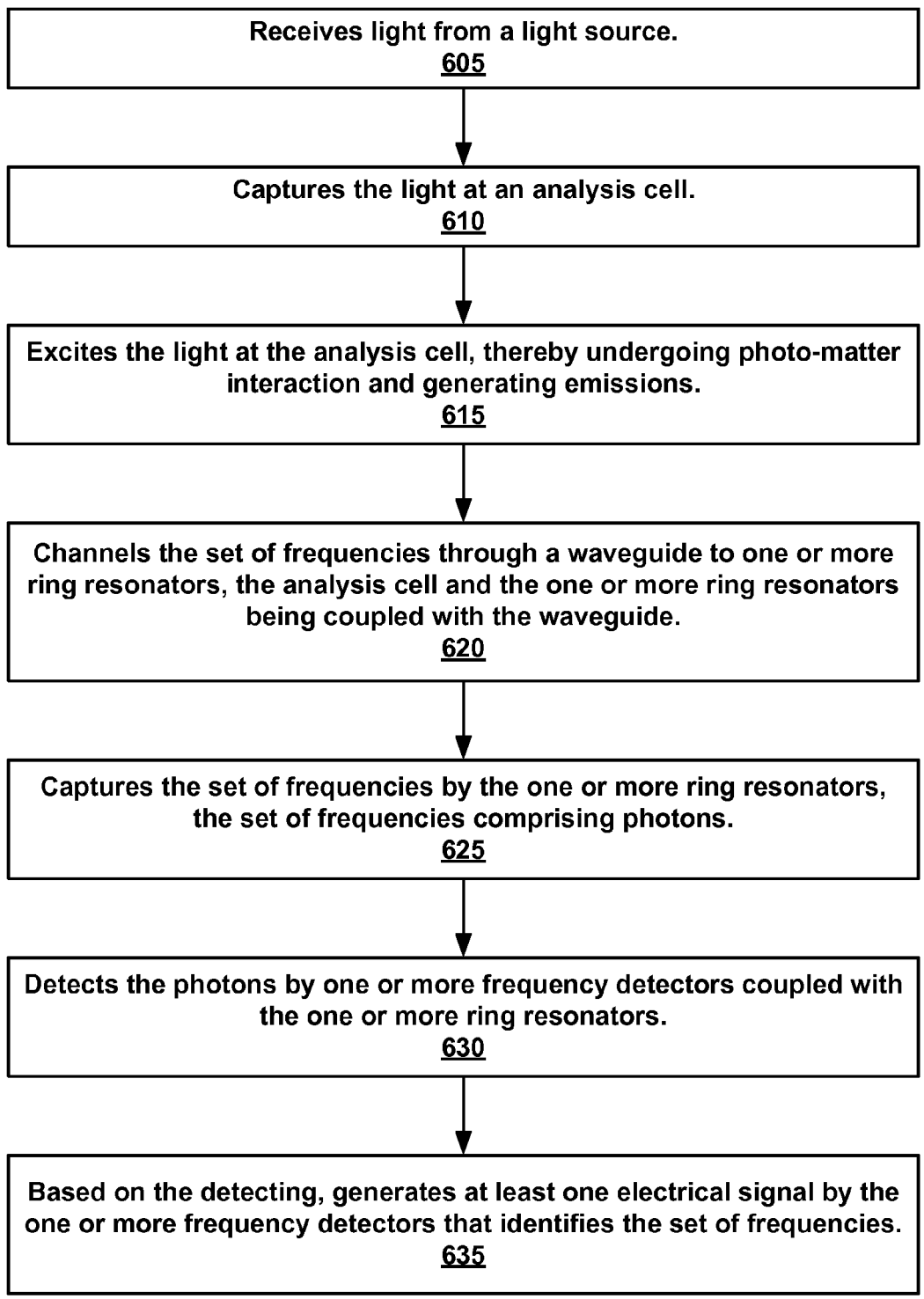
FIG. 6 illustrates an example method for improving Raman detection efficiency, in accordance with an embodiment of the present technology.

FIG. 6 shows an example method for improving Raman detection efficiency, in accordance with an embodiment of the present technology. Referring to 605 of FIG. 6, in one embodiment light 115 is received from a light source 120. Referring now to 610 of FIG. 6, in one embodiment, light 115 is then captured at an analysis cell 105. Referring now to 615 of FIG. 6, light 115 is then excited at the analysis cell 105, thereby generating photon-matter interaction. The photon-matter interaction involves a set of frequencies.

Referring now to 620 of FIG. 6, in one embodiment, the set of frequencies are then channeled through a waveguide 130 to one or more ring resonators 150a-150c. The analysis cell 105 and the one or more ring resonators 150a-150c are coupled with waveguide 130. Referring now to 625 of FIG. 6, the one or more ring resonators 150a-150c then capture the set of frequencies. The set of frequencies comprise photons.

Referring now to 630 of FIG. 6, in one embodiment, frequency detectors 155a-155c detect the photons. The frequency detectors 155a-155c are coupled with the one or more ring resonators 150a-150d. Referring now to 635 of FIG. 6, based on the detecting, at least one electrical signal 160a-160d is generated by the one or more frequency detectors 155a-155d, thereby identifying the set of frequencies.

Thus, embodiments of the present technology enable the improved sensitivity of the Raman detection.

Various embodiments of the present invention are thus described. While the present invention has been described in particular embodiments, it should be appreciated that the present invention should not be construed as limited by such embodiments, but rather construed according to the following claims.

What is claimed is:

1. A compact sensor system comprising:
an analysis cell configured for photon-matter interaction, where photons are received from a light source; and
an integrated-optical spectral analyzer configured for identifying a set of frequencies, said integrated-optical spectral analyzer comprising:
a waveguide coupled with said analysis cell, said waveguide comprising a first end and a second end and one or more ring resonator integration sites therebetween, wherein a first end of said waveguide is coupled with said analysis cell, said waveguide configured for propagating said set of frequencies through said waveguide from said analysis cell to said second end;
one or more ring resonators coupled with said one or more ring resonator integration sites of said waveguide, said one or more ring resonators comprising a predetermined bandwidth and configured for capturing said set of frequencies corresponding to frequencies within said predetermined bandwidth; and
one or more frequency detectors coupled with said one or more tunable ring resonators, said one or more frequency detectors configured for generating electrical signals that identify each of said set of frequencies.

2. The compact sensor system of claim 1, wherein said waveguide is optically coupled via a lens with said analysis cell, said lens coupled with said first end of said waveguide and configured for capturing said luminescence generated by said analysis cell.

3. The compact sensor system of claim 1, wherein said analysis cell comprises an integrated device, said integrated device comprising:
an array of nanostructures comprising a material, wherein said material is configured to allow light to pass through;
Surface Enhanced Raman Spectroscopy active nanoparticles disposed on at least a portion of said array of nanostructures; and
an optical component integrated below a base of said array of nanostructures, wherein said optical component is configured to enhance light interaction with said array of nanostructures.

4. The compact sensor system of claim 3, further comprising:
a resonant grating integrated below a base of said array of nanostructures, wherein said resonant grating is configured to establish a guided-mode resonance with light passing through said material.

5. The compact sensor system of claim 3, wherein said optical component comprises one or more mirrors.

6. The compact sensor system of claim 1, wherein said array of nanostructures are substantially cone-shaped.

7. The compact sensor system of claim 1, wherein said array of nanostructures are substantially columnar.

8. The compact sensor system of claim 1, wherein said photon-matter interaction comprises a Raman emission.

9. The compact sensor system of claim 1, wherein said photon-matter interaction comprises a fluorescence emission.

10. The compact sensor system of claim 1, wherein said ring resonator comprises a circular shape.

11. The compact sensor system of claim 1, wherein said one or more ring resonators comprising a predetermined bandwidth is tunable such that said predetermined bandwidth may be changed to be a bandwidth different from said predetermined bandwidth.

12. The compact sensor system of claim 1, wherein said waveguide is comprised of silicon oxide.

13. The compact sensor system of claim 1, wherein said light source is a solid state laser.

14. The compact sensor system of claim 1, wherein the coupling of said one or more tunable ring resonators with said waveguide and the coupling of said one or more frequency detectors with said one or more tunable ring resonators is accomplished via one or more waveguide connectors.

15. A monolithic integrated optical spectrometer comprising:
a waveguide comprising a first end and a second end and one or more ring resonator integration sites therebetween, wherein a first end of said waveguide is coupled with a resonant grating of an integrated device of an analysis cell, said waveguide configured for propagating a set of frequencies through said waveguide from said integrated device to said second end, wherein said integrated device is configured for enhancing electrical signals in Surface Enhanced Raman Spectroscopy, said integrated device comprising:
an array of nanostructures comprising a material, wherein said material is configured to allow light to pass through;
Surface Enhanced Raman Spectroscopy active nanoparticles disposed on at least a portion of said array of nanostructures;
a mirror integrated below a base of said array of nanostructures, wherein said mirror is configured to enhance light interaction with said array of nanostructures; and
wherein said resonant grating is integrated below a base of said array of nanostructures and is configured to establish a guided-mode resonance with light passing through said material;
one or more tunable ring resonators coupled with said one or more ring resonator integration sites of said waveguide, said one or more tunable ring resonators comprising a predetermined bandwidth and configured for capturing said set of frequencies corresponding to frequencies within said predetermined bandwidth; and
one or more frequency detectors coupled with said one or more tunable ring resonators, said one or more frequency detectors configured for generating electrical signals that identify each of said set of frequencies.

16. A method for improving Raman detection efficiency, said method comprising:
receiving light from a light source;
capturing said light at an analysis cell;
exciting light at said analysis cell, thereby undergoing photon-matter interaction and generating emissions;
channeling a set of frequencies through a waveguide to one or more ring resonators, said analysis cell and said one or more ring resonators being coupled with said waveguide;
capturing said set of frequencies by said one or more ring resonators, said set of frequencies comprising photons;
detecting said photons by one or more frequency detectors coupled with said one or more ring resonators; and
based on said detecting, generating at least one electrical signal by said one or more frequency detectors that identifies said set of frequencies.

* * * * *